United States Patent [19]

Bucca et al.

[11] Patent Number: 5,679,818

[45] Date of Patent: Oct. 21, 1997

[54] INORGANIC ARYLACETYLENIC MONOMERS

[75] Inventors: Daniel Bucca; Teddy M. Keller, both of Alexandria, Va.

[73] Assignee: The United States of America as represented by the Secretary of the Navy, Washington, D.C.

[21] Appl. No.: 687,880

[22] Filed: Jul. 26, 1996

[51] Int. Cl.$^6$ .................. C07F 5/02; C07F 7/08
[52] U.S. Cl. .......... 556/403; 556/431; 556/432; 556/433; 556/434; 556/489; 549/4; 549/213; 549/214; 546/13; 546/14
[58] Field of Search .................. 556/403, 431, 556/432, 433, 434, 489; 549/214, 213; 546/13, 14; 549/4

[56] References Cited

U.S. PATENT DOCUMENTS

| | | | |
|---|---|---|---|
| 3,354,193 | 11/1967 | Fein et al. | 556/403 |
| 3,355,478 | 11/1967 | Fein et al. | 556/403 X |
| 3,733,298 | 5/1973 | Knollmueller | 556/403 X |
| 4,111,999 | 9/1978 | Beard et al. | 556/403 X |

*Primary Examiner*—Paul F. Shaver
*Attorney, Agent, or Firm*—Thomas E. McDonnell; John J. Karasek

[57] ABSTRACT

The present invention is a compound having the formula:

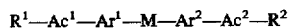

where $R^1$ and $R^2$ are independently selected from the group consisting of hydrogen, unsubstituted alkyl groups, substituted alkyl groups, unsubstituted aryl groups, and substituted aryl groups, where $Ac^1$ and $Ac^2$ are independently selected alkynyl groups having at least 1 carbon-carbon triple bond, where $Ar^1$ and $Ar^2$ are independently selected substituted or unsubstituted aromatic diradicals, and where M has the structure

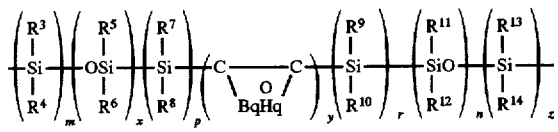

where m is a positive integer, wherein x, p, y, r, n, and z are independently selected integers, where $z \neq 0$ when $n \neq 0$, and where $R^3$ through $R^{14}$ are independently selected from the group consisting of hydrogen, unsubstituted alkyl groups, substituted alkyl groups, unsubstituted aryl groups, and substituted aryl groups.

34 Claims, 12 Drawing Sheets

Where M is:  a= —Si(CH3)2OSi(CH3)2CB10H10CSi(CH3)2OSi(CH3)2— b= —Si(CH3)2OSi(CH3)2— c= —Si(CH3)2—

INORGANIC ARYLACETYLENIC MONOMERS

BACKGROUND OF THE INVENTION

1. Field of the Invention

The present invention relates to monomers suitable for polymerization to high temperature thermosets, and more particularly to monomers containing silane and/or siloxane groups, aryl groups, acetylene groups, and optionally carborane groups.

2. Description of the Related Art

Thermoset polymers that are stable at high temperatures are a goal of the art. A great deal of research has been performed to date on developing precursor oligomers and polymers that may be converted to thermosets, and further pyrolyzed to carbon or ceramics depending upon the starting materials.

Monomer precursors for thermosets are desired, due to their improved processibility. Monomer precursors usually will be liquid at room temperature, or will melt at low temperatures (i.e., will be low melting solids), and will have controllable viscosity. Broader processing windows, another goal of the art, may also be found with monomer precursors and blends of these precursors.

Other desired features of precursors for thermosets include high char yield and low evolution of volatiles.

SUMMARY OF THE INVENTION

Accordingly, it is an object of this invention to provide monomers that have a large processing window (e.g., in excess of 200° C.), are low melting, and are highly soluble in commercially available solvents.

It is a further object of this invention to provide such monomers that can be converted to products that are stable at high temperatures.

These and additional objects of the invention are accomplished by the structures and processes hereinafter described.

The present invention is a compound having the formula:

$$R^1-Ac^1-Ar^1-M-Ar^2-Ac^2-R^2$$

where $R^1$ and $R^2$ are independently selected from the group consisting of hydrogen, unsubstituted alkyl groups, substituted alkyl groups, unsubstituted aryl groups, and substituted aryl groups, where $Ac^1$ and $Ac^2$ are independently selected alkynyl groups having at least 1 carbon-carbon triple bond, where $Ar^1$ and $Ar^2$ are independently selected substituted or unsubstituted aromatic diradicals, and where M has the structure where m is a positive integer, wherein x, p, y, r, n, and z are independently selected integers, where z≠0 when n≠0, and where $R^3$ through $R^{14}$ are independently selected from the group consisting of hydrogen, unsubstituted alkyl groups, substituted alkyl groups, unsubstituted aryl groups, and substituted aryl groups.

The structure in the foregoing formula denotes a carboranyl group.

BRIEF DESCRIPTION OF THE DRAWINGS

A more complete appreciation of the invention will be obtained readily by reference to the following Description of the Preferred Embodiments and the accompanying drawings in which like numerals in different figures represent the same structures or elements, wherein.

DETAILED DESCRIPTION OF THE PREFERRED EMBODIMENTS

The following are incorporated by reference herein, in their entireties, and for all purposes:

(a) U.S. Pat. No. 5,483,017, for "High Temperature Thermosets and Ceramics Derived from Linear Carborane-(Siloxane or Silane)-Acetylene Copolymers", issued Jan. 9, 1996 to Keller et al (hereinafter Keller '017), (b) U.S. patent application Ser. No. 08/540,148, for "High Temperature Ceramics Derived from Linear Carborane-(Siloxane or Silane)-Acetylene Copolymers", filed Oct. 6, 1995 by Keller et al. (hereinafter Keller '148 application), and (c) U.S. patent application Ser. No. 08/687,700 for "Thermoset Polymers From Inorganic Arylacetylenic Monomers", filed Jul. 26, 1996 Bucca et al., and designated Navy Case No. 77,459.

The monomers of the present invention contain a group near the center of the molecule (designated "M" in the formula above), where this group contains at least a silane moiety, and optionally also any of the following: additional silane moieties, siloxane moieties, carborane moieties, and combinations thereof. The monomers of the present invention also contain two aromatic groups (designated $Ar^1$ and $Ar^2$ in the formula above) on either side of the "M" group, two alkynyl groups (designated $Ac^1$ and $Ac^2$ in the formula above) bonded to the aromatic groups, and two terminal groups (designated $R^1$ and $R^2$ in the formula above).

Preferred "M" Groups

Depending on the particular properties desired, skilled practitioners will select appropriate values for m, n, p, q, r, x, y, and z.

Preferably, m is a positive integer between 1 and 15, inclusive. Preferably, x is an integer between 0 and 10, inclusive. Preferably, p is an integer between 0 and 10, inclusive. Preferably, y is an integer between 0 and 10, inclusive. Preferably, r is an integer between 0 and 10, inclusive. Preferably, n is an integer between 0 and 10, inclusive. Preferably, z is an integer between 0 and 10, inclusive. More preferably, m, x, p, y, r, n, and z are not more than 5.

Varying the ratio of carborane to silane groups can vary the properties of the monomer. More siloxane groups will lead to a lower melting point and therefore a broader processing window. More carboranyl groups will lead to better oxidative resistance. See Keller '148 application.

Preferred "M" groups include one or more silane moieties, one or more siloxane moieties, and one or more carboranyl moieties, and combinations thereof.

It is preferred to have at least one silane group interposed between any siloxane groups in M and the aryl groups $Ar^1$ and $Ar^2$, so that the oxygens in the siloxane groups are not directly bonded to the aryl groups. Accordingly, when $x\neq0$, $m\neq0$. Likewise, when $n\neq0$, $z\neq0$. In some circumstances it will be preferred to have M consist only of silane (and optionally siloxane) moieties. For such embodiments, $y=0$, and the proportions of m, x, and p (or equivalently r, n, and z) are adjusted to give the desired proportions of silane to siloxane.

In the structure q and q' are independently selected integers from 3 to 16, inclusive. Suitable carboranyl groups are 1,7-dodecacarboranyl, 1,10-octacarboranyl, 1,6-octacarboranyl, 2,4-pentacarboranyl, 1,6-tetracarboranyl, 9-alkyl-1,7-dodecacarboranyl, 9,10-dialkyl-1,7-dodecacarboranyl, 2-alkyl-1,10-octacarboranyl, 8-alkyl-1,6-octacarboranyl, decachloro-1,7-dodecacarboranyl, octachloro-1,10-octacarboranyl, decafluoro-1,7-dodecacarboranyl, octafluoro-1,10-octacarboranyl, closo-dodeca-ortho-carboranyl, closo-dodeca-meta-carboranyl, closo-dodeca-para-carboranyl, and combinations thereof.

Good results have been obtained with compounds having $m=x=y=z=n=1$ and $p=r=0$ (designated herein as M moiety a), having $m=x=1$ and $y=z=n=p=r=0$ (designated herein as M moiety b), and having $m=1$ and $x=y=z=n=p=r=0$ (designated herein as M moiety c).

Preferred "Ar" Groups $Ar^1$ and $Ar^2$ may be the same or different. Suitable Ar groups include substituted or unsubstituted phenyl, substituted or unsubstituted naphthalene radical, substituted or unsubstituted anthracene radical, substituted or unsubstituted phenanthrene radical, and substituted or unsubstituted pyrine radical. Other suitable Ar groups include aromatic groups having at least one heterocycle. Appropriate heterocycles include substituted or unsubstituted pyridine, substituted or unsubstituted pyrole, substituted or unsubstituted furan, and substituted or unsubstituted thiophene.

Preferred Ar groups are substituted or (more preferably) unsubstituted aromatic diradicals having 4 or fewer aromatic rings.

It is preferred to have the Ar groups bonded to the M groups and the Ac groups at non-adjacent sites, to minimize stearic effects. For example, in the case of an Ar group having a single aromatic ring (such as a group), it is preferred to have the M and Ac groups at meta or para positions to each other. Meta substitution typically provides better polymerizing and/or processing properties, while para substitution typically provides better thermal properties.

Preferred "Ac" Groups $Ac^1$ and $Ac^2$ may be the same or different. As shown infra, a range of acetylenic groups are within the scope of the present invention. Preferred Ac groups have 10 or fewer carbons.

Ac groups may have one carbon-carbon triple bond. Ac groups may have two or more carbon-carbon triple bonds. In the case where the Ac groups have two or more triple bonds, two or more of these bonds may be conjugated. Alternatively, these two or more carbon-carbon triple bonds may be unconjugated. In the case where the adjacent terminal R group is H or phenyl (i.e., $R^1$ in the case of $Ac^1$ and $R^2$ in the case of $Ac^2$), the preferred Ac group is $—C\equiv C—$. In the case where the adjacent terminal R group is the Ac group can be $—C\equiv C—C\equiv C—$.

Preferred "R" Groups $R^1$ and $R^2$ may be the same or different. Suitable R groups include unsubstituted alkyl groups, hydrogen, and unsubstituted aryl groups. Typical R groups include hydrogen, unsubstituted alkyl groups having 10 or fewer carbons, substituted alkyl groups having 10 or fewer carbons, unsubstituted aryl groups having 10 or fewer carbons, and substituted aryl groups having 10 or fewer carbons.

More typical R groups include alkyl groups and aryl groups, substituted with one or more halide or —OH groups. Preferred R groups include primary, secondary, and tertiary alkyl groups. More preferred R groups are taken from the group consisting of H, phenyl, substituted phenyl, substituted or unsubstituted alkyl having 6 or fewer carbons, substituted or unsubstituted benzyl, substituted or unsubstituted naphthalene radical, substituted or unsubstituted anthracene radical, substituted or unsubstituted phenanthrene radical, and substituted or unsubstituted pyrine radical.

H-terminated monomers will tend to react at lower temperatures and therefore provide higher char yields. Aryl-terminated monomers (especially phenyl-terminated monomers) will tend to have broader processing windows.

Synthetic Routes

Figure 1:
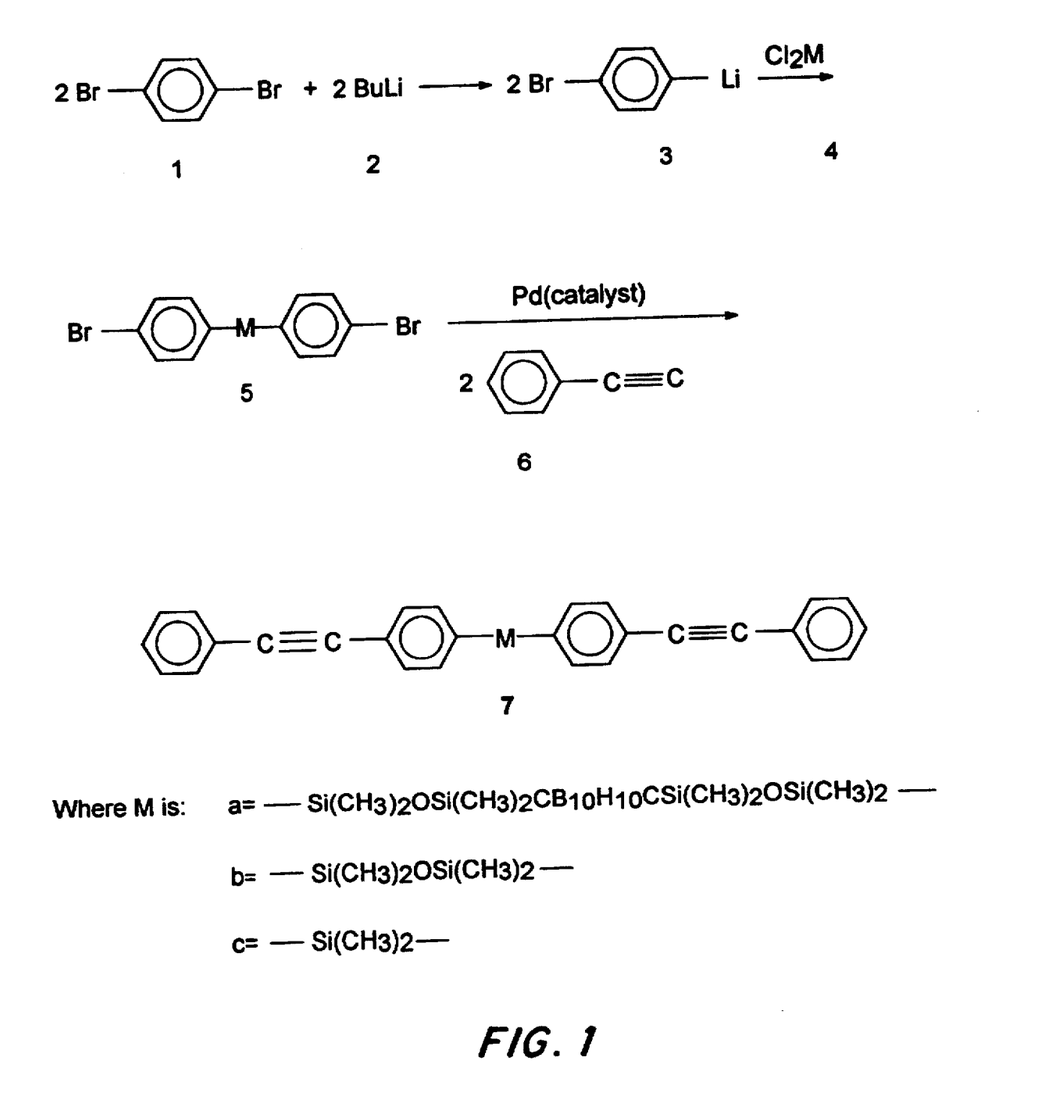
FIG. 1 shows an exemplary synthesis of compounds according to the present invention.

An exemplary synthesis is depicted in FIG. 1. As shown, an aryl dihalide (in this case, p-dibromobenzene) 1 undergoes a substitution reaction with n-butyllithium 2 to form a lithium aryl halide 3 (in this case, p-bromolithium benzene). 1,n-Dichlorinated M 4 (for the desired M group in the final product) reacts with the Li moieties in 3 to produce M with substituted bromoaryl groups in the 4 and 4' positions. The aryl groups correspond to the desired Ar groups in the final product.

This dihalide 5 is then reacted (typically with a Pd catalyst) with an acetylenic compound 6 containing the desired terminal group R and acetylenic group Ac, to yield the desired monomer 7.

To vary the aryl halide groups, e.g., to put a bromophenyl group in the 4 position, and a bromonapthalenyl group in the 4' position, and in turn vary the Ar groups in the monomer so that $Ar^1 \neq Ar^2$, one would first add one equivalent of p-bromolithium benzene to the 4,4' dichlorinated M4 to produce a monochlorinated M4 with an aryl halide group in the 4 position. Then the addition of the second lithium aryl halide (lithium bromonapthalenyl) would yield the desired 4-bromophenyl,4'-bromonaphthalenyl M4. The notations "4" and "4'" in the foregoing example represent the substituent positions at opposite ends of the molecule or group. For example:

This is notation is adopted as a convenience, for illustrative purposes.

To vary the terminal R groups, mixtures of various substituted primary acetylenic compounds can be used in the above synthesis.

To make H-terminated monomers, heating a dibromide precursor inside a bomb, with acetylene and a catalyst is an effective synthetic route.

Figure 2:
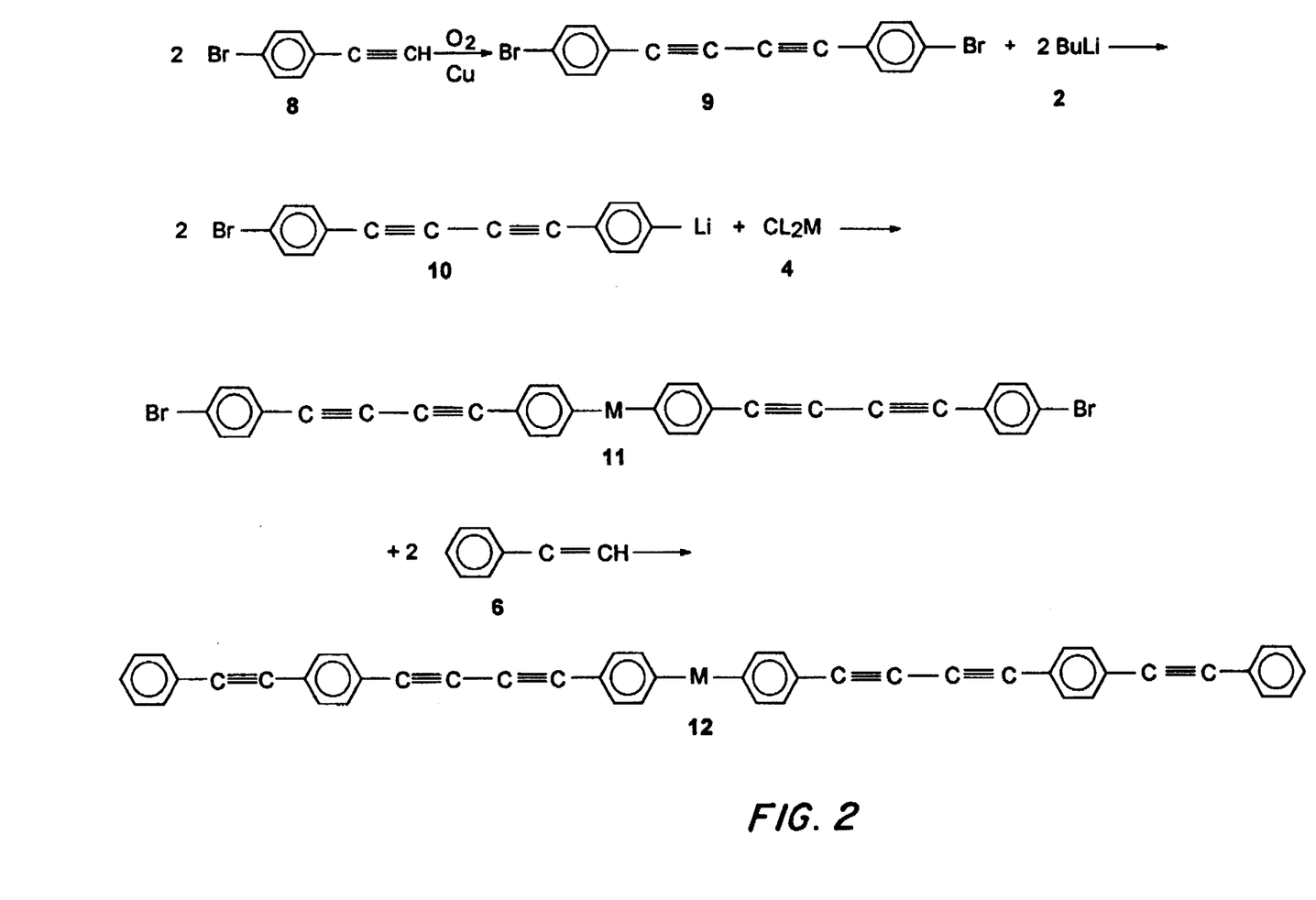
FIG. 2 shows another exemplary synthesis of compounds according to the present invention.
Figure 3:
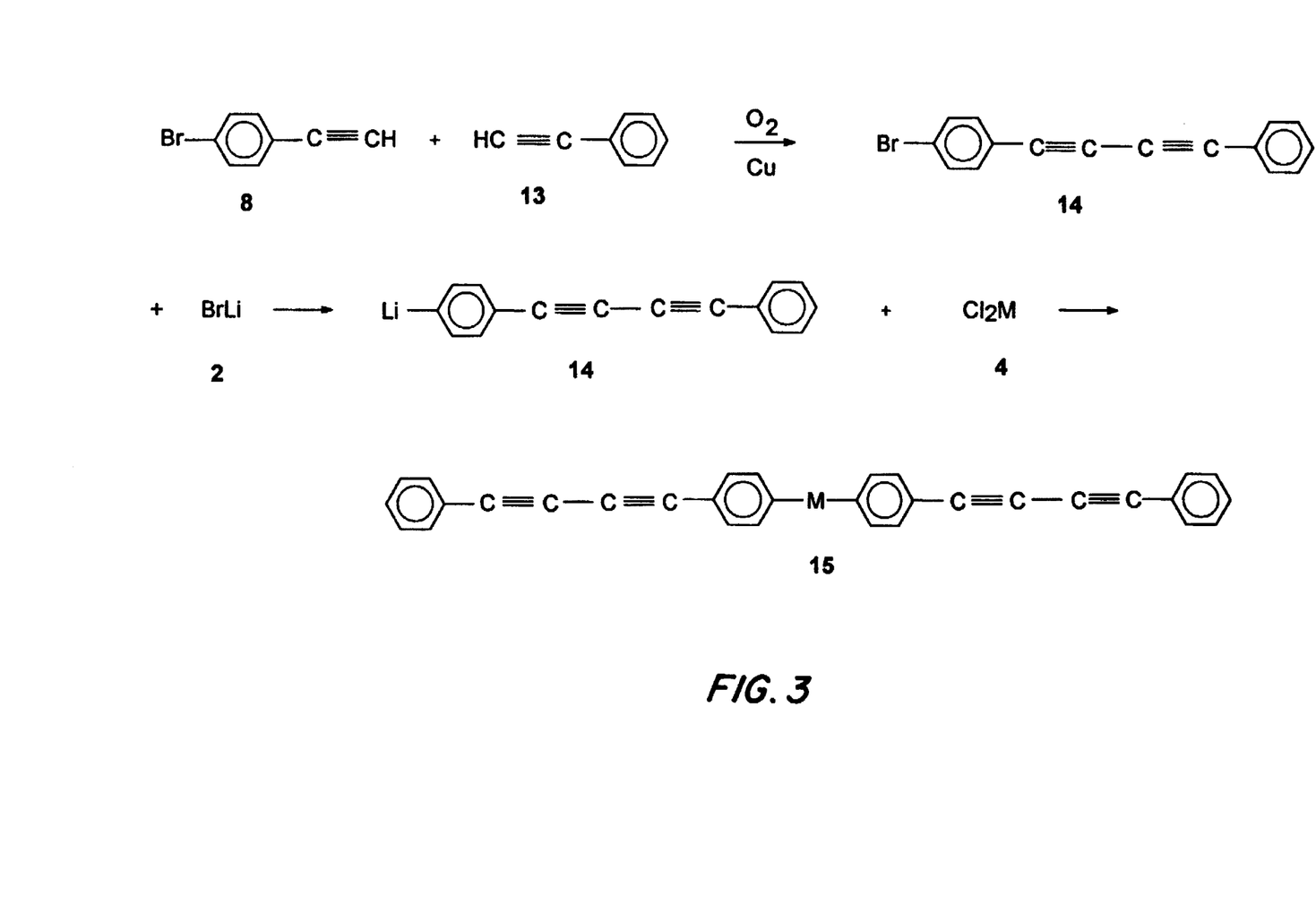
FIG. 3 shows another exemplary synthesis of compounds according to the present invention.

If more than one —C≡C— moiety is desired in the monomer of the invention, different synthetic routes may be employed. For example, as shown in FIG. 2, monomers with multiple acetylene groups and multiple aromatic rings can be synthesized. Another synthetic route is shown in FIG. 3. Of course, skilled practitioners will be able to modify the foregoing synthetic routes, using the knowledge of a person of ordinary skill in the art.

EXAMPLES

Having described the invention, the following examples are given to illustrate specific applications of the invention, including the best mode now known to perform the invention. These specific examples are not intended to limit the scope of the invention described in this application.

Example 1

1,7-Bis(4-bromophenyltetramethyldisiloxyl)-m-carborane (5a)

A 100-mL three-necked round bottomed flask was equipped with two addition funnels and a stir bar and was charged with 1.75 g (7.42 mmol) of 1,4-dibromobenzene and 30 mL of dry THF. The flask was equilibrated at −78° C. and 3.0 mL (7.5 mmol) of n-butyllithium in hexane was added dropwise through the first addition funnel, which caused the formation of a white precipitate. After the mixture had been stirred for 45 min, 1.6 mL (3.5 mmol) of 1,7-bis(chlorotetramethyldisiloxyl)-m-carborane (4a) was added through the second addition funnel causing the milky white mixture to change to a clear yellow solution. This solution was warmed to room temperature, then poured into cold aqueous ammonium chloride and extracted with ether. The organic layer was separated, washed with water, dried over anhydrous sodium sulfate, and the solvent removed by rotary evaporation. The product (5a, 2.37 g, 93% yield) was a clear-colorless-viscous liquid and appeared pure by $^1$H NMR. $^1$H NMR (in CDCl$_3$): 7.48 (doublet of doublets, 2H, aromatic); 7.35 (doublet of doublets, 2H, aromatic); 3.1 (broad, 10H, BH); 0.34 (s, 12H, CH$_3$); 0.12 (s, 12H, CH$_3$). $^{13}$C NMR (CDCl$_3$): 137.7, 135.7, 134.5, 131.0 (aromatic); 68.27 (Si—C—B); 0.52 (Si—C).

Example 2

Synthesis of 1,7-Bis(4phenylethynylphenyltetramethyldisiloxyl)-m-carborane (7a)

A 100-mL three-necked, round bottomed flask was equipped with a condenser and stir bar and charged with 60 mL of degassed triethylamine, 2.37 g (3.30 mmol) of 1,7-bis(4-bromophenyl-tetramethyldisiloxyl)-m-carborane (5a), 1.1 mL (10 mmol) of phenylacetylene, 66 mg (0.094 mmol) of bis(triphenylphosphine)palladium(II) chloride, 250 mg (0.954 mmol) of triphenylphosphine, and 96 mg (0.502 mmol) of copper (I) iodide. The mixture was stirred and heated at reflux for 12 h, resulting in the formation of a white precipitate. The reaction mixture was then cooled to room temperature, the precipitate filtered and the solvent removed by rotary evaporation. The resulting solid was taken up in ether, washed with dilute aqueous HCl, dried over anhydrous sodium sulfate and the solvent removed by rotary evaporation to afford an orange solid (7a). The solid was recrystallized from isopropanol yielding a light yellow powder (1.92 g, 58% yield). $^1$H NMR (in CDCl$_3$): 7.49 (m, 12H, aromatic); 7.31 (m, 6H, aromatic); 3.1-1.2 (b, 10H, BH); 0.34 (s, 12H, CH$_3$); 0.13 (s, 12H, CH$_3$). $^{13}$C NMR (CDCl$_3$): 39.3, 132.8, 131.6, 130.8, 128.3, 124.3, 123.2 (aromatic); 90.1, 89.4 (acetylene); 68.39 (Si—C—B); 0.46 (Si—C).

Example 3

Bis(4-bromophenyl)tetramethyldisiloxane (5b)

This compound was prepared in a similar manner as 5a by combining 1,4-dibromobenzene (10 g, 42 mmol) with n-butyllithium (20 mL, 50 mmol) and 1,3-dichlorotetramethyldisiloxane (4.6 mL, 22 mmol). Purification of 5b was achieved by vacuum distillation to afford a colorless-viscous liquid (60% yield). $^1$H NMR (CDCl$_3$): 7.52 (doublet of doublets, 8H, aromatic), 0.34 (s, 12H, CH$_3$).

Example 4

Bis(4-phenylethynylphenyl)tetramethyldisiloxane (7b)

This compound was prepared in a similar manner as 7a by combining compound 5b (3.0 g, 6.8 mmol) with phenylacetylene (2.3 g, 23 mmol) and the catalyst combination: bis(triphenylphosphine)palladium(II) chloride (200 mg 0.3 mmol), triphenylphosphine (400 mg, 1.6 mmol), and copper (I) iodide (100 mg, 0.6 mmol). Purification of 7b was achieved by dissolution in methylene chloride and passing the concentrated solution through a column of silica. A light brown solid (7b, 1.33 g, 56% yield) was recovered. $^1$H NMR (CDCl$_3$): 7.53 (m, 12H, aromatic); 7.35 (m, 6H, aromatic); 0.36 (s, 12H, CH$_3$).

Example 5

Bis(p-bromophenyl)dimethylsilane (5c)

A 100 mL three-neck flask was equipped with an addition funnel, condenser, and stir bar. The flask was flame dried, flushed with argon and charged with magnesium (1.04 g, 42.8 mmol) and 5 mL of dry ether. A few drops of 1,2-dibromoethane was added to activate the magnesium and caused the ether to reflux. p-Dibromobenzene (10 g, 42.4 mmol) in 40 mL of ether was added dropwise at such a rate as to maintain reflux. After complete addition, the reaction mixture was heated to maintain reflux for an additional five hours. Upon cooling to room temperature copper cyanide (0.1 g, 1.1 mmol) was introduced. The reaction mixture was then cooled to 0 C. and dichlorodimethylsilane (2.55 g, 19.8 mmol) was added dropwise through the addition funnel causing the reaction to warm slightly. The reaction mixture was stirred overnight at room temperature. The product mixture was poured over ice and the organic layer was separated and dried over anhydrous sodium sulfate. The ether was removed by vacuum and a yellow oily solid was recovered. The crude product (5c) was fractionally sublimed under full vacuum. The first fraction contained non-reacted dibromobenzene and 2.6 g (36% yield) of 5c was collected for the second fraction. $^1$H NMR (in CDCl$_3$): d, 7.47 ppm 4H; d, 7.32 ppm 4H; s, 0.51 ppm 6H.

Example 6

Bis(p-phenylethynylphenyl)dimethylsilane (7c)

A 50 mL three-neck flask equipped with a stir bar, gas inlet, and reflux condenser was charged with 35 mL of triethylamine and bis(p-bromophenyl)dimethylsilane 5c (1.07 g, 2.89 mmol). Argon was bubbled through the solution for 20 min. Phenylacetylene (0.96 g, 9.40 mmol) was added and the solution was degassed for an additional 10 min. Bis(triphenylphosphine)palladium(II) chloride (0.115 g, 0.164 mmol), triphenylphosphine (0.180 g, 0.686 mmol) and copper(I) iodide (0.116 g, 0.607 mmol) were mixed together and added to the reaction flask. The flask was placed in a oil bath set at 90° C. and the solvent was heated to reflux for 4 hr. A white precipitate formed during the course of the reaction, which was separated by suction filtration and characterized as the hydrogen bromide/amine by-product (1.05 g, 92% yield of by-product). The mother liquor was diluted with ether, washed with 10% HCl, dried over sodium sulfate. The solvent was removed under vacuum and an orange solid (7c) was recovered. The solid was purified by crystallization from a ethanol/water mixture to leave a light tan solid, mp 134 C. 1H NMR (in CDCl$_3$): two broad peaks, 7.5 ppm and 7.3 ppm 18H; s, 0.58 ppm 6H.

Figure 4:
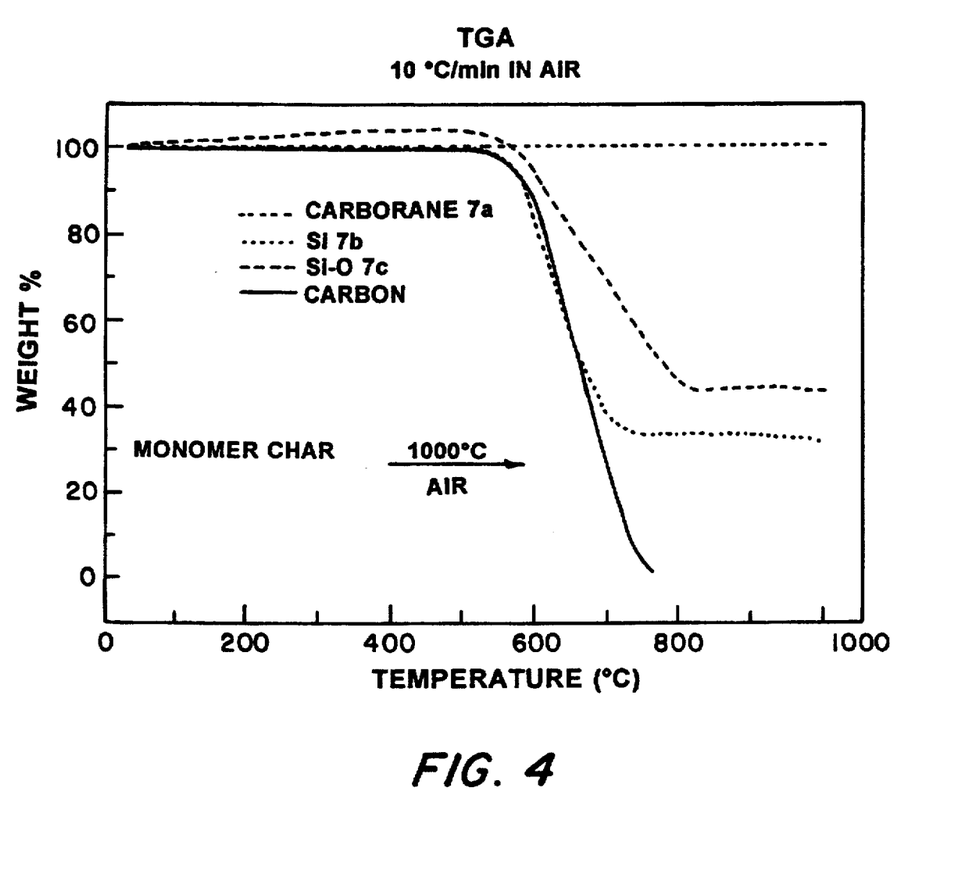
FIG. 4 shows the TGA of three compounds according to the invention.
Figure 5:
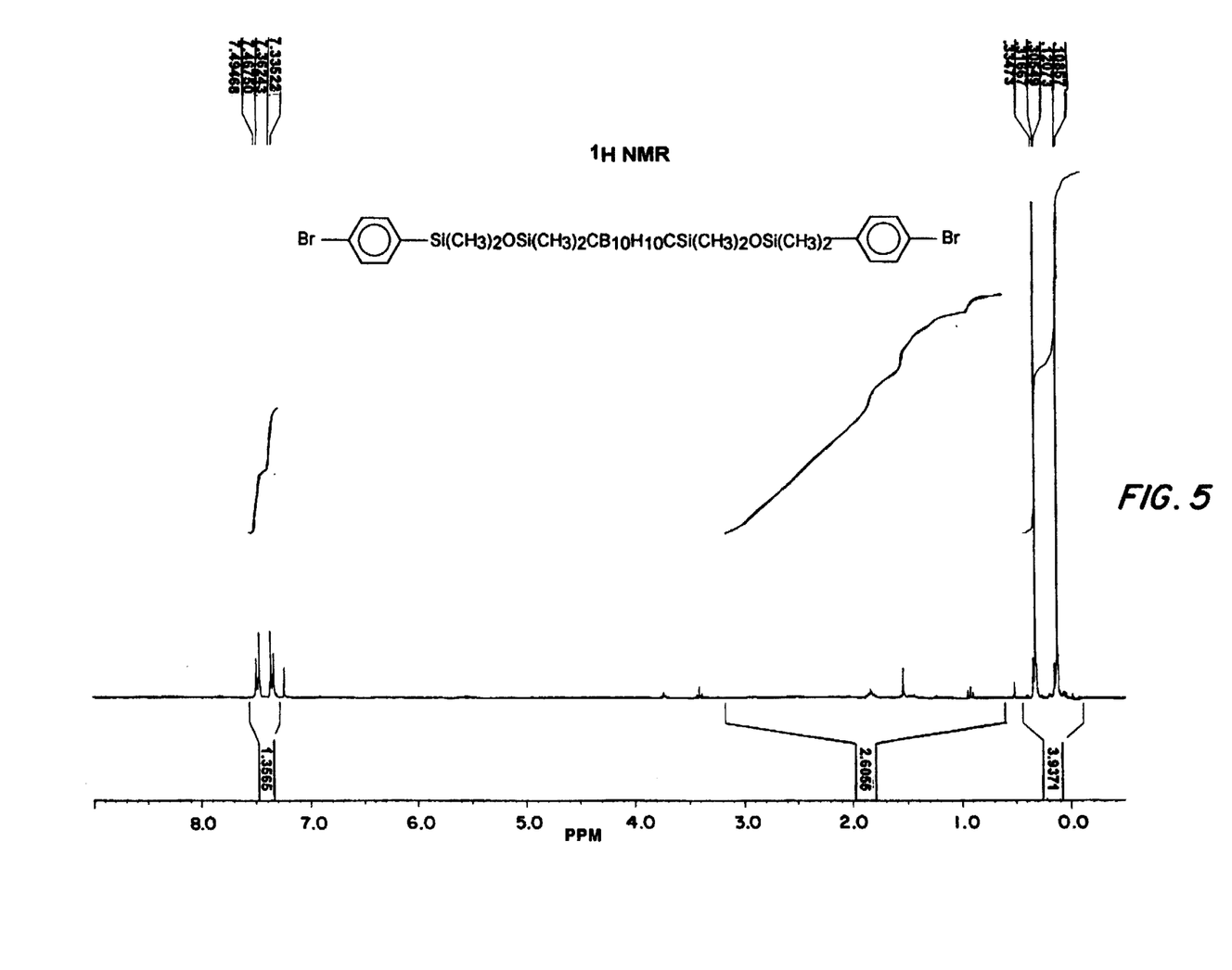
FIGS. 5 through 12 show the $^1$H NMR of seven compounds according to the invention.
Figure 6:
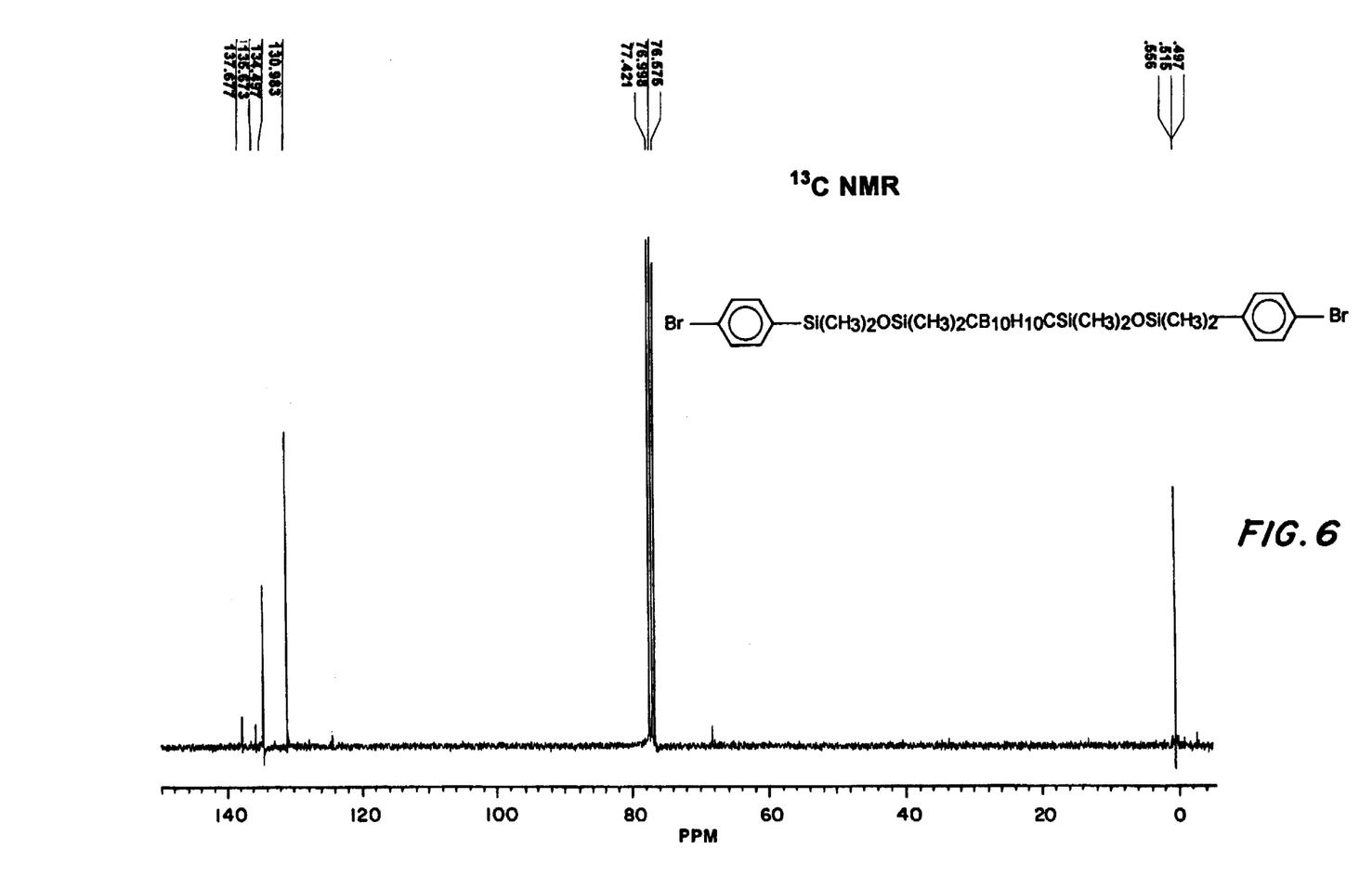
Figure 7:
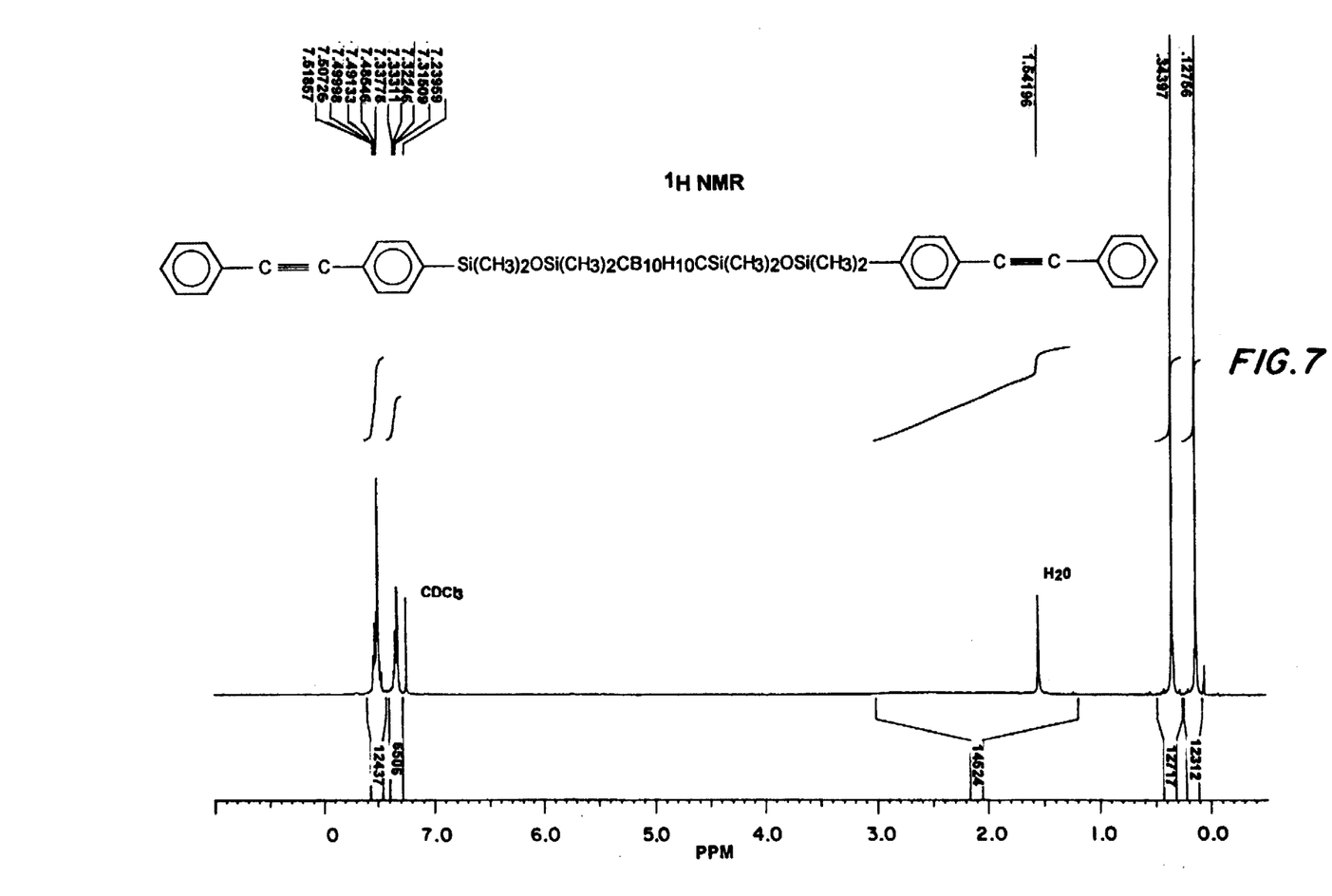
Figure 8:
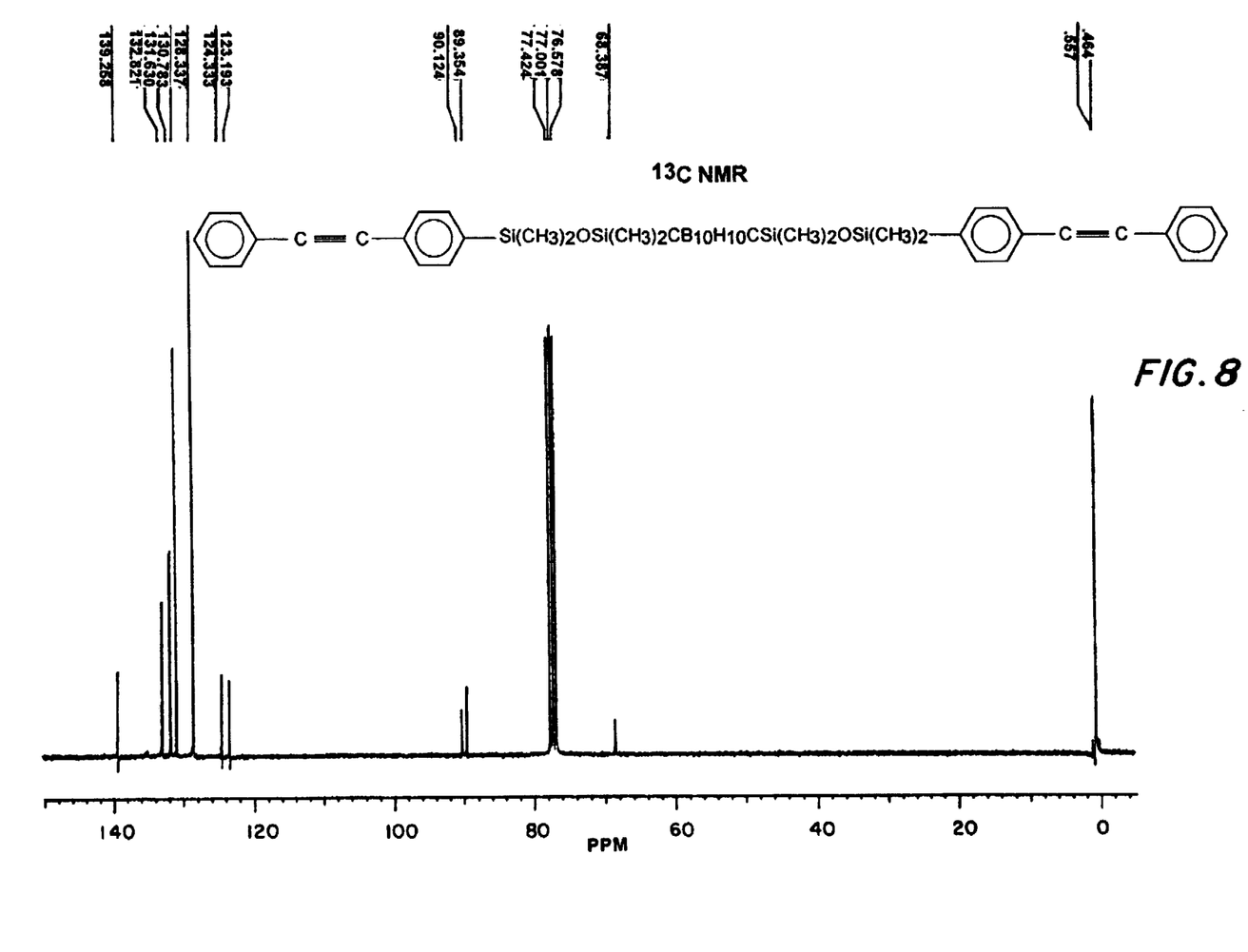
Figure 9:
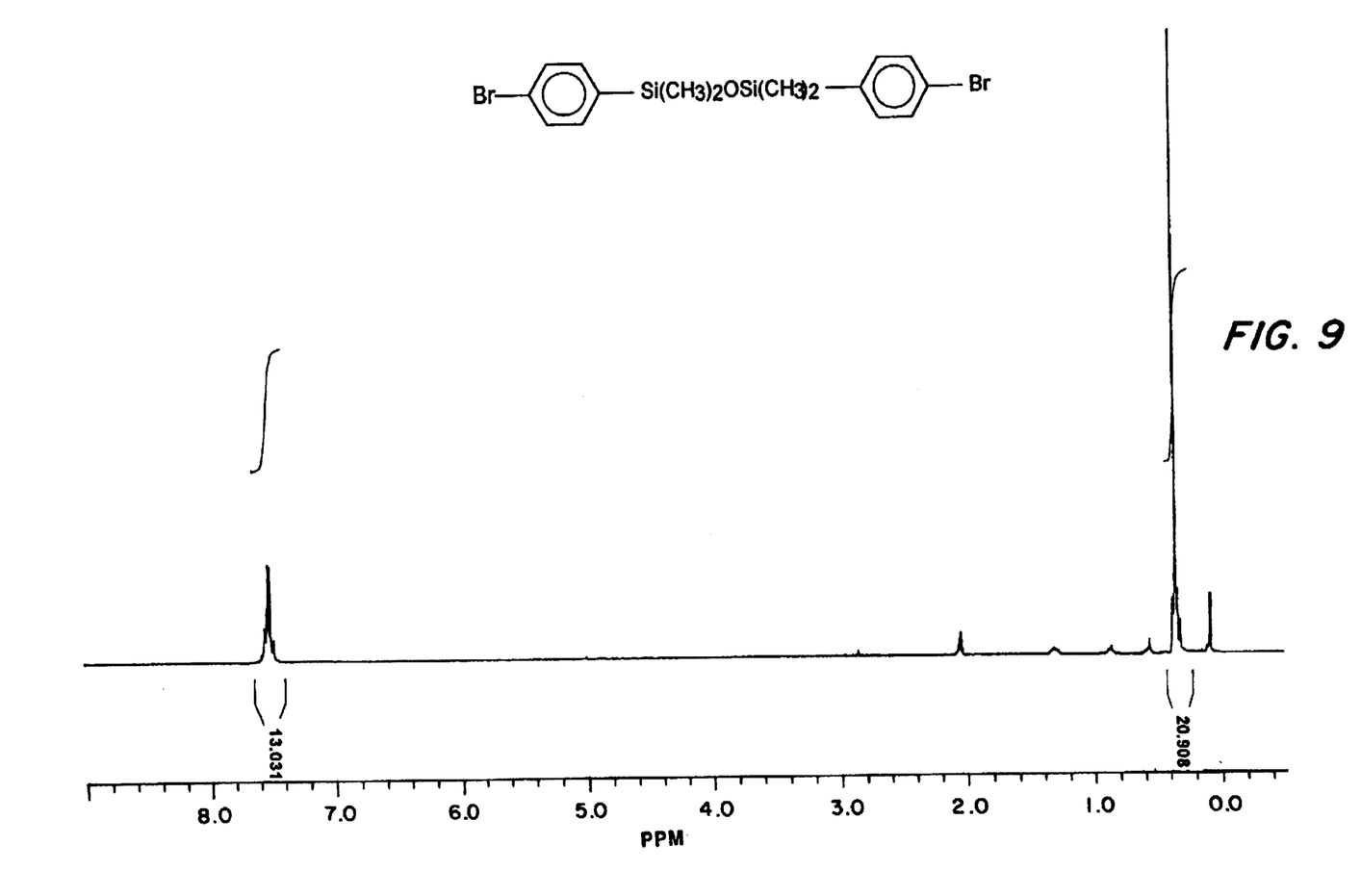
Figure 10:
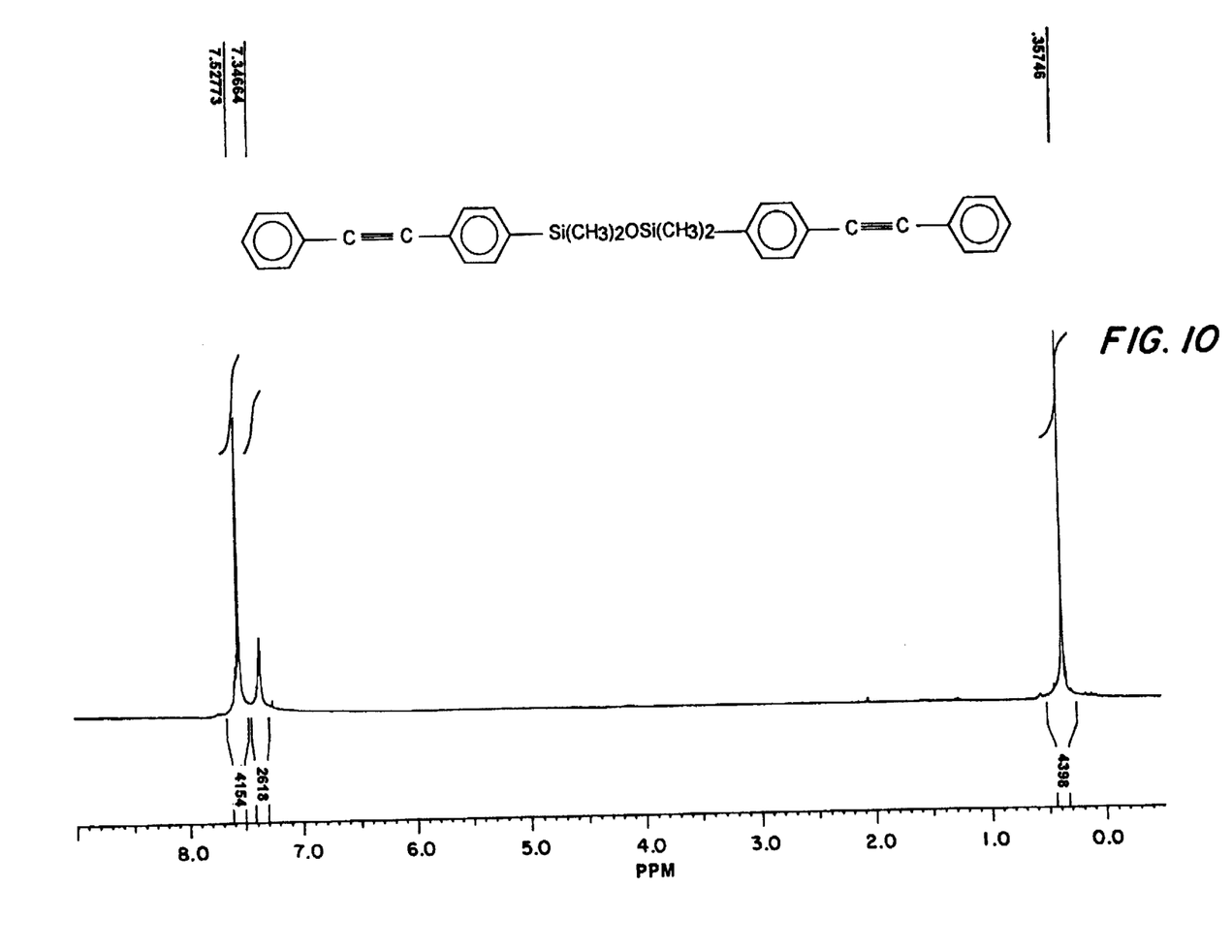
Figure 11:
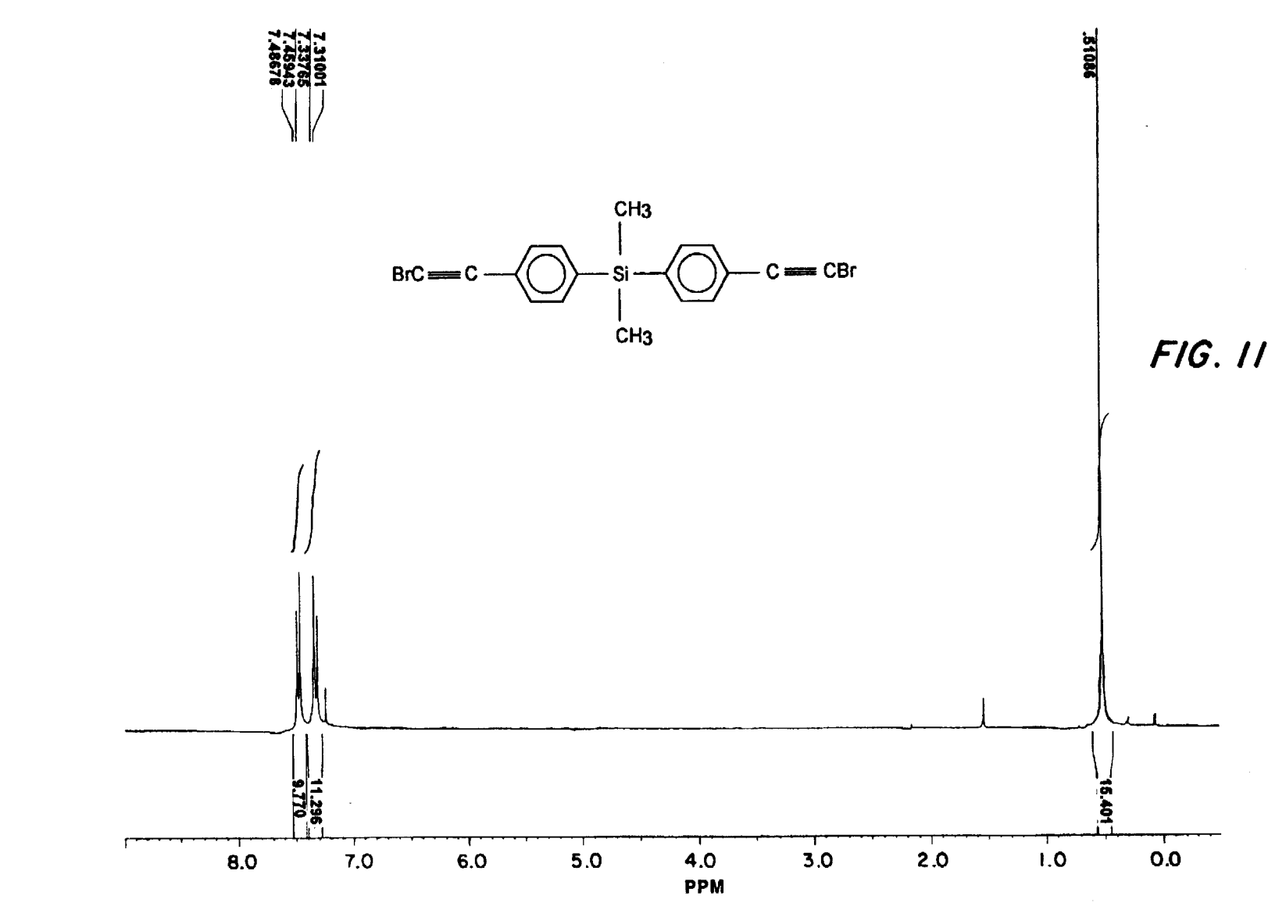
Figure 12:
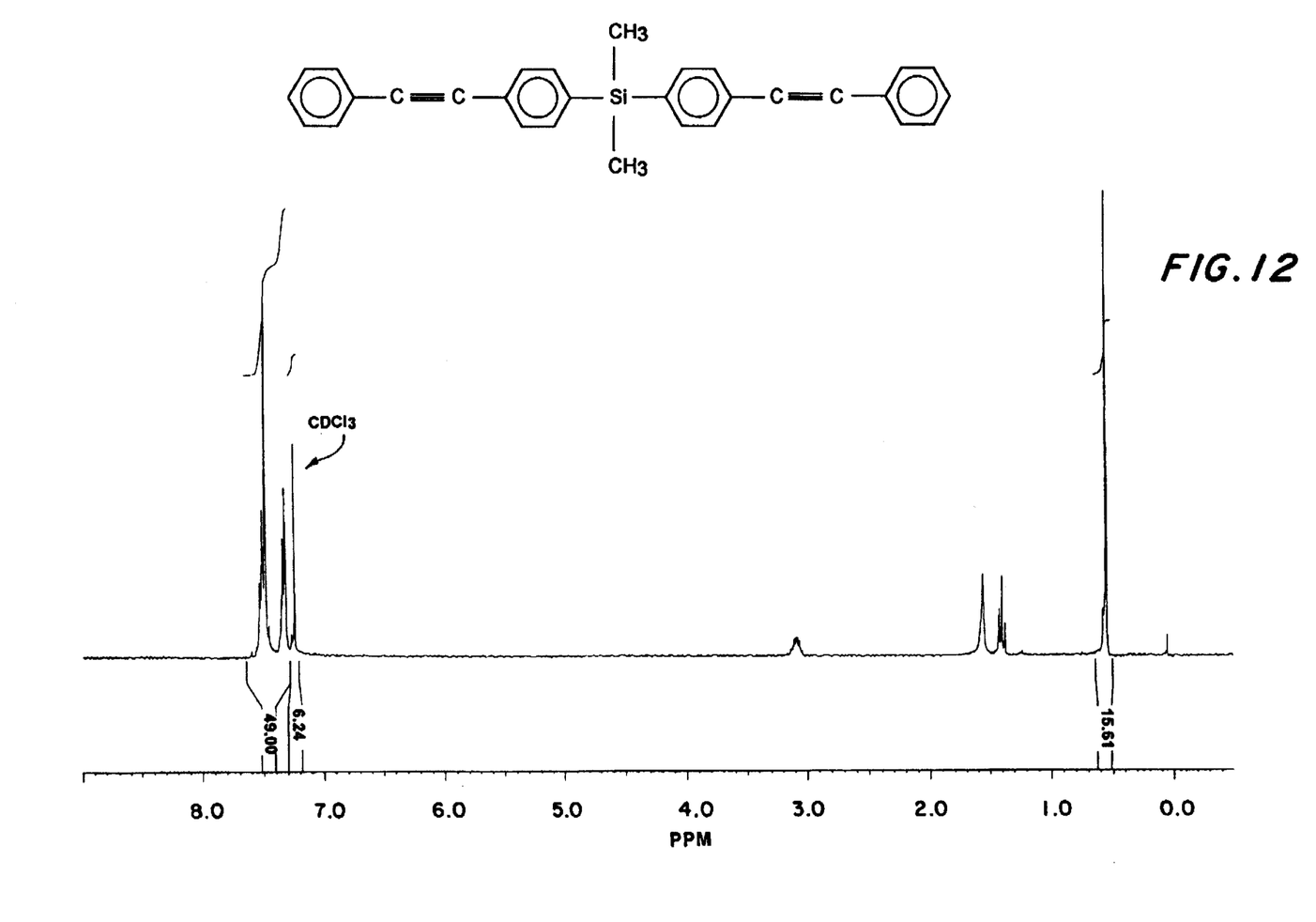

The TGAs of 7a–c are shown in FIG. 4.

The $^1$H NMR spectra of selected compounds according to the invention are shown in FIGS. 5 through 12.

Obviously, many modifications and variations of the present invention are possible in light of the above teachings. It is therefore to be understood that, within the scope of the appended claims, the invention may be practiced otherwise than as specifically described.

What is claimed is:

1. A chemical compound having the formula:

wherein R$^1$ and R$^2$ are independently selected from the group consisting of hydrogen, unsubstituted alkyl groups, substituted alkyl groups, unsubstituted aryl groups, and substituted aryl groups;

wherein Ac$^1$ and Ac$^2$ are independently selected alkynyl groups having at least 1 carbon-carbon triple bond;

wherein Ar$^1$ and Ar$^2$ are independently selected substituted or unsubstituted aromatic diradicals; and wherein M has the structure wherein m is a positive integer, x is an integer, p is an integer, y is an integer, r is an integer, n is an integer, inclusive, z is an integer, and z≠0 when n≠0, and wherein R$^3$ through R$^{14}$ are independently selected from the group consisting of hydrogen, unsubstituted alkyl groups, substituted alkyl groups, unsubstituted aryl groups, and substituted aryl groups.

2. The compound of claim 1, wherein m is a positive integer between 1 and 15, inclusive.

3. The compound of claim 1, wherein x is an integer between 0 and 10, inclusive.

4. The compound of claim 1, wherein p is an integer between 0 and 10, inclusive.

5. The compound of claim 1, wherein y is an integer between 0 and 10, inclusive.

6. The compound of claim 1, wherein r is an integer between 0 and 10, inclusive.

7. The compound of claim 1, wherein n is an integer between 0 and 10, inclusive.

8. The compound of claim 1, wherein z is an integer between 0 and 10, inclusive.

9. The compound of claim 1, wherein R$^1$ and R$^2$ have 10 or fewer carbons.

10. The compound of claim 1, wherein at least one of R$^1$ and R$^2$ is H.

11. The compound of claim 1, wherein R$^1$ and R$^2$ are H.

12. The compound of claim 1, wherein Ac$^1$ and Ac$^2$ have 10 or fewer carbons.

13. The compound of claim 1, wherein Ar$^1$ and Ar$^2$ have 4 or fewer aromatic rings.

14. The compound of claim 1, wherein R$^3$ through R$^{14}$ are independently selected from the group consisting of hydrogen, CH$_3$, C$_2$H$_5$, and C$_3$H$_7$.

15. The compound of claim 1, wherein p=r=0, y is 0, 1, or 2, and z is 1 or 2.

16. The compound of claim 1, wherein p=r=0, y is 0 or 1, and z is 1.

17. The compound of claim 1, wherein p=r=0, x is an integer between 1 and 5, inclusive, y is 1, and z is 1.

18. The compound of claim 1, wherein p=r=x=y=n=z=0.

19. The compound of claim 1, wherein x=y=z=1.

20. The compound of claim 1, wherein x=1 and y=n=z=0.

21. The compound of claim 1, wherein R$^1$ and R$^2$ are independently selected from the group consisting of unsubstituted alkyl groups and unsubstituted aryl groups.

22. The compound of claim 1, wherein R$^1$ and R$^2$ are independently selected from the group consisting of alkyl groups and aryl groups, substituted with one or more halide or —OH groups.

23. The compound of claim 1, wherein R$^1$ and R$^2$ are independently selected from the group consisting of primary alkyl groups.

24. The compound of claim 1, wherein R$^1$ and R$^2$ are independently selected from the group consisting of secondary alkyl groups.

25. The compound of claim 1, wherein R$^1$ and R$^2$ are independently selected from the group consisting of tertiary alkyl groups.

26. The compound of claim 1, wherein R$^1$ and R$^2$ are independently selected from the group consisting of H, phenyl, substituted phenyl, substituted or unsubstituted alkyl having 6 or fewer carbons, substituted or unsubstituted naphthalene radical, substituted or unsubstituted anthracene radical, substituted or unsubstituted phenanthrene radical, and substituted or unsubstituted pyrine radial.

27. The compound of claim 1, wherein R$^1$ and R$^2$ are independently selected aromatic groups having at least one heterocycle.

28. The compound of claim 27, wherein said aromatic groups having at least one heterocycle are selected from the group consisting of substituted or unsubstituted pyridine, substituted or unsubstituted pyrole, substituted or unsubstituted furan, and substituted or unsubstituted thiophene.

29. The compound of claim 1, wherein $Ac^1$ and $Ac^2$ are independently selected alkynyl groups having 1 carbon-carbon triple bond.

30. The compound of claim 1, wherein $Ac^1$ and $Ac^2$ are independently selected alkynyl groups having two or more carbon-carbon triple bonds, which may be conjugated or unconjugated.

31. The compound of claim 1, wherein $Ac^1$ and $Ac^2$ are independently selected from the group consisting of —C≡C— and —C≡C—C≡C—.

32. The compound of claim 1, wherein $Ar^1$ and $Ar^2$ are independently selected from the group consisting of substituted or unsubstituted phenyl, substituted or unsubstituted naphthalene radical, substituted or unsubstituted anthracene radical, substituted or unsubstituted phenanthrene radical, and substituted or unsubstituted pyrine radial.

33. The compound of claim 1, wherein $Ar^1$ and $Ar^2$ are independently selected aromatic groups having at least one heterocycle.

34. The compound of claim 33, wherein said aromatic groups having at least one heterocycle are selected from the group consisting of substituted or unsubstituted pyridine, substituted or unsubstituted pyrole, substituted or unsubstituted furan, and substituted or unsubstituted thiophene.

* * * * *